United States Patent
Lattner

(10) Patent No.: US 7,384,985 B2
(45) Date of Patent: Jun. 10, 2008

(54) PROCESS FOR PRODUCING METHANOL

(75) Inventor: James R. Lattner, LaPorte, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 36 days.

(21) Appl. No.: 11/484,308

(22) Filed: Jul. 11, 2006

(65) Prior Publication Data

US 2007/0021514 A1    Jan. 25, 2007

Related U.S. Application Data

(60) Provisional application No. 60/700,805, filed on Jul. 20, 2005.

(51) Int. Cl.
*C07C 27/00* (2006.01)
(52) U.S. Cl. ............ 518/706; 518/713; 518/714; 518/715
(58) Field of Classification Search ............ 518/706, 518/713–715
See application file for complete search history.

(56) References Cited

U.S. PATENT DOCUMENTS 4,670,473 A    6/1987 Walker et al.
4,968,722 A    11/1990 Westerterp
5,219,891 A    6/1993 Sie
5,449,696 A    9/1995 Dandekar et al.
6,723,886 B2   4/2004 Allison et al.

FOREIGN PATENT DOCUMENTS

GB    2 255 516    11/1992

OTHER PUBLICATIONS

Dark A.M.; "*Methanol Loop Design*", Nitrogen, British Sulphur Co., London, GB, No. 215, pp. 36-38; May 1995.

*Primary Examiner*—Jafar Parsa

(57) ABSTRACT

This invention is directed to a process for producing methanol. The methanol product that is produced according to this invention is achieved with a high conversion of synthesis gas. The high conversion of synthesis gas is achieved by flowing a liquid layer across a plurality of catalyst beds countercurrent to the gas flow. The gas containing methanol product exiting each bed flows through the liquid layer. The liquid acts to extract methanol from the gas, as well as cool the gas.

23 Claims, 1 Drawing Sheet

PROCESS FOR PRODUCING METHANOL

CROSS REFERENCE TO RELATED APPLICATIONS

This application claims the benefit of Provisional Application No. 60/700,805 filed Jul. 20, 2005, the disclosure of which is fully incorporated herein by reference.

FIELD OF INVENTION

This invention relates to the production of methanol. In particular, this invention relates to the production of methanol using countercurrent flow of liquid and gases.

BACKGROUND OF THE INVENTION

In general, the methanol synthesis process predominantly relies on synthesis gas (syngas) as feed components. Syngas generally contains carbon monoxide and hydrogen. Carbon dioxide and nitrogen can also be present. Methanol production using syngas basically involves the following reactions:

$$CO + 2H_2 \rightarrow CH_3OH \quad (1)$$

$$CO_2 + 3H_2 \rightarrow CH_3OH + H_2O \quad (2)$$

An additional side reaction includes:

$$CO + H_2O \leftrightarrow CO_2 + H_2 \quad (3)$$

Methanol synthesis is a strongly exothermic and equilibrium-limited reaction. Increases in reaction temperature tend to disfavor methanol formation, and tend to deactivate some of the more commonly used copper based catalysts. Thus, control of equilibrium in this complex reaction scheme is important to maximize the amount of methanol formed.

U.S. Pat. No. 4,968,722 discloses that two types of reactors are typically used for methanol synthesis: adiabatic bed reactor and cooled (i.e., isothermal) reactors. Adiabatic bed reactors typically have several fixed catalyst beds in series, and the temperature is controlled with heat exchangers between beds or by introducing cold synthesis gas between beds. Isothermal reactors typically have a bundle of tubes filled with catalyst, and use water to cool the tubes as the reaction takes place.

In the '722 patent, a particular reaction system is detailed in which the system uses multiple reactors in series. After each reactor, an absorption vessel is used to absorb methanol from the reactor effluent. Examples of absorbents used include tetra ethylene glycol dimethyl ether (TEGDME), sulfolane, and 18-crown-6.

U.S. Pat. No. 5,219,891 discloses a fluidized bed reactor that is used to make methanol. The reactor has catalyst in a plurality of interconnected fluidized bed sections, and each section is cooled by a heat exchanger. The temperature in the highest section is reduced to below the highest temperature in a lower section.

U.S. Pat. No. 5,449,696 discloses a process for production of methanol that uses a simulated moving bed. In the process, the carbon monoxide and hydrogen are catalytically reacted to form methanol. The methanol is separated from unreacted carbon monoxide and hydrogen by concurrent adsorption, using the carbon monoxide and hydrogen as the desorbent.

U.S. Pat. No. 6,723,886 discloses a process for production of methanol in a catalytic distillation unit, or CDU. This patent discloses that a number of stages can be used to achieve a final conversion of CO approaching 100%. The heat of reaction may be removed by removing a portion of the methanol, cooling it, and returning it to the CDU. It is not disclosed how the unreacted reactants are returned to the catalyst zone by distillation, since the syngas components are essentially non-condensable at methanol synthesis conditions.

A variety of reaction processes have been disclosed in an effort to find efficient ways of controlling equilibrium and/or temperatures in the complex methanol reaction process. Additional process schemes are still desired in order to maximize the conversion of CO, $CO_2$ and hydrogen to methanol in much simpler and more effective ways.

SUMMARY OF THE INVENTION

This invention provides a process for producing methanol in a manner that provides for high conversion of syngas in a single pass with excellent control of gas phase compositions and reaction temperatures. In particular, the process enables the reaction to be carried out at relatively low temperatures and allows for efficient recovery of the methanol product. A liquid flowing in an overall countercurrent direction to the reactant gas is used to control the temperature and gas composition of the reaction process.

According to one aspect of the invention, there is provided a process for producing methanol that includes flowing gas containing carbon monoxide, carbon dioxide and hydrogen through a plurality of beds of methanol synthesis catalyst so as to form methanol in the flowing gas. The gas exiting each of the beds is flowed through separate liquid layers containing methanol to remove at least a portion of the methanol from the gas and cool the gas. Preferably, the separate liquid layers are flowed in an overall countercurrent direction relative to the flowing gas, and the flow of at least one liquid layer is across an upper portion of a corresponding catalyst bed. In one embodiment, a methanol product is recovered from any one or more of the liquid layers.

In another embodiment, the method also includes cooling at least a portion of the recovered methanol product. Preferably, at least a portion of the cooled methanol product is added to at least one of the liquid layers flowing in countercurrent direction relative to the gas compositions.

In one embodiment, each liquid layer is at an average temperature that cools the gas flowing through it. Preferably, each liquid layer is at an average temperature of not greater than 250° C. Preferably, each bed has average temperature in a linear arrangement or profile that differs from one another in a range of from 0° C. to 10° C.

In another aspect, the invention provides a process for producing methanol that comprises flowing gas containing carbon monoxide, carbon dioxide and hydrogen through a bed of methanol synthesis catalyst to form gas containing methanol. The gas containing methanol is flowed through a liquid layer containing methanol to remove at least a portion of the methanol from the flowing gas and also cool the gas. Preferably, the liquid layer is flowed substantially horizontally across an upper portion of the catalyst bed as the gas flowing through the catalyst bed flows in a substantially vertical direction. Optionally, the gas from which at least a portion of the methanol has been removed is flowed through a second bed of methanol synthesis catalyst to form a second gas containing methanol, and methanol product is recovered from the liquid layer.

In another embodiment of the invention, the methanol synthesis catalyst includes an oxide of at least one element selected from the group consisting of copper, silver, zinc, boron, magnesium, aluminum, vanadium, chromium, manganese, gallium, palladium, osmium and zirconium.

In an optional embodiment, the liquid layer contains at least one additional methanol adsorbent selected from the group consisting of water, monohydric alcohols, and polyhydric alcohols. In a preferred embodiment of the invention, the methanol is formed at an approach to equilibrium temperature of not greater than 15° C. Preferably, the gas and liquid streams are flowed in a vessel at a pressure of at least 30 bar.

In another embodiment of the invention, the gas is flowed at a weight hourly space velocity of not greater than 100 $hr^{-1}$. Preferably, the cooled gas that exits the liquid layer has an average temperature of not greater than 210° C. In a typical embodiment, the methanol is continued to form until overall conversion of the carbon monoxide is at least about 50%.

The liquid is preferably flowed across a bed of catalyst or in a horizontal direction relative to the gas. In one embodiment, the gas is flowed at a gas velocity that achieves a pressure drop through the catalyst bed of at least 0.01 psi/ft of bed height.

BRIEF DESCRIPTION OF THE DRAWING

An example of one specific embodiment of this invention in shown in the attached FIG. 1, wherein the FIG. 1 is a flow diagram of a vessel in which gas is flowed across a series of catalyst beds and liquid is flowed in a countercurrent direction to the gas.

DETAILED DESCRIPTION OF THE INVENTION

Figure 1:
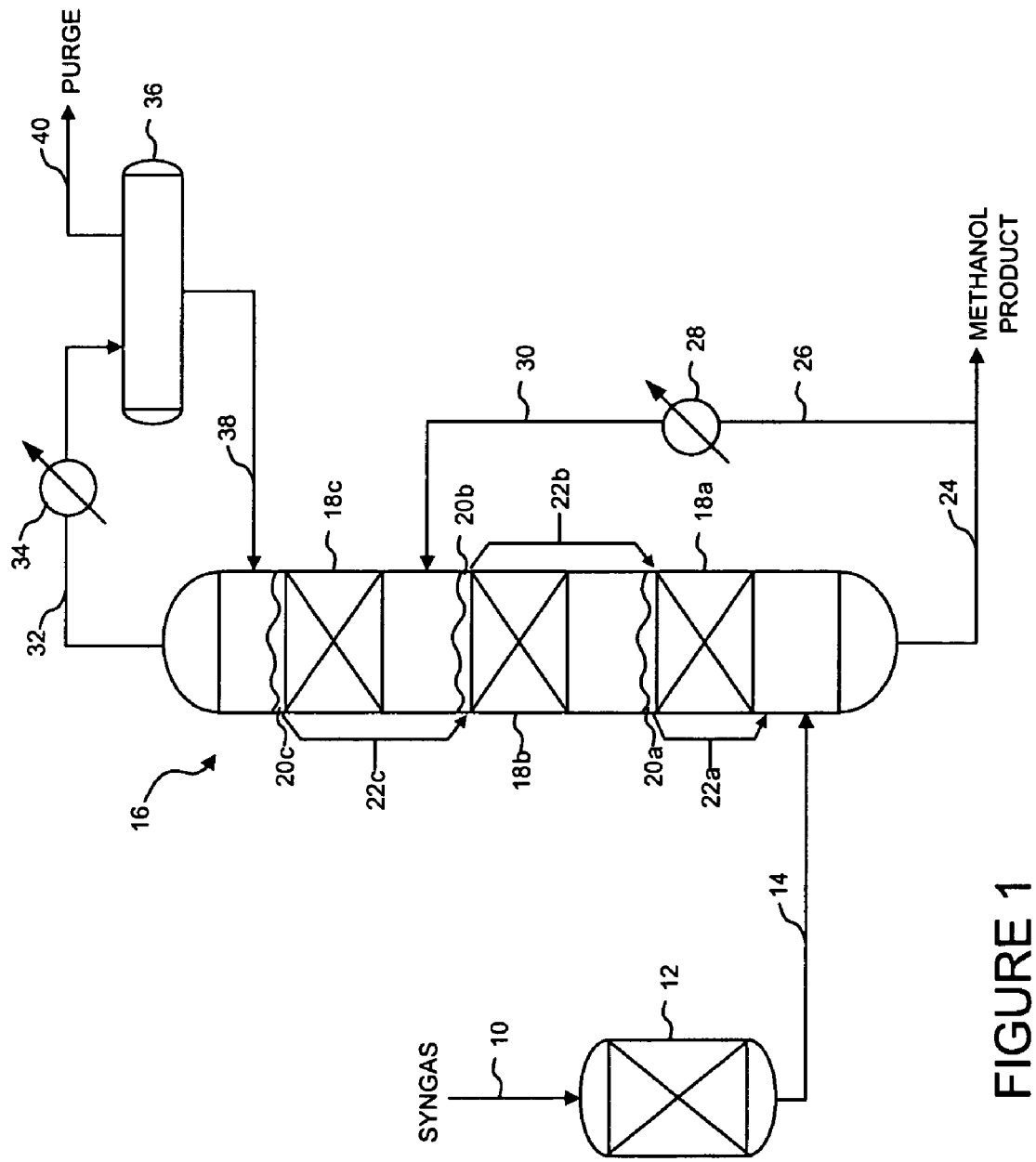

I. Methanol Production Using Multiple Catalyst Beds

This invention is directed to a process for producing methanol. The process utilizes a plurality of beds of methanol synthesis catalyst to form methanol product from synthesis gas (syngas).

The syngas conversion that is achieved according to this invention is very high. The high conversions are achieved by flowing a liquid layer over each catalyst bed so that gas product coming off each bed flows through the liquid layer. The liquid layer acts as a methanol extractant to remove methanol from the gas emerging from the bed of catalyst, leaving any unreacted synthesis gas component behind, and also acts to cool the gas. This cooled gas is then sent to the next bed of catalyst to continue the methanol production reaction, and similar extraction using a liquid layer is repeated, until the reaction is essentially complete. The absorption of methanol into the liquid phase upon leaving each catalyst bed removes at least a portion, preferably at least a majority, of methanol from the synthesis gas. The synthesis gas flowing to the next catalyst bed is cooler and reduced in methanol concentration, thus providing a renewed thermodynamic driving force to allow further conversion of the syngas.

The synthesis gas contains in greater part carbon oxides, such as carbon monoxide, and hydrogen. As these components are flowed through a bed of catalyst, they are converted to methanol. The methanol is formed in the gas phase as the syngas flows through the bed of catalyst.

In general, the process involves flowing gas containing synthesis gas components through a plurality of beds of methanol synthesis catalyst. At least 3, preferably at least 5, and most preferably at least 10 beds of methanol synthesis catalyst are used. As overall conversion of the syngas components progresses, the temperature profile as the gas flows through the plurality of beds of methanol synthesis catalyst remains fairly consistent. On an average linear basis, i.e., from one bed to the next, the average temperature of each bed changes very little. In one embodiment, the average temperature of each bed in a linear arrangement or profile differs from one another in a range of from 0° C. to 10° C., preferably from 0° C. to 5° C., and more preferably from 0° C. to 3° C.

As the gas passes through a catalyst bed, the exothermic reaction causes the gas to heat up. In one embodiment, the gas exits each bed at a temperature of at least 190° C., preferably at least 200° C., and more preferably at least 210° C. The methanol content of the gas exiting any one bed will be higher than that of the gas that entered that particular bed. Preferably, the methanol concentration of the gas exiting each bed is at least 50 mol%, preferably at least 55 mol%, and more preferably at least 60 mol%. This enriched gas stream is contacted with the liquid layer that is flowing across a top portion of the catalyst bed. This contacting cools the gas, absorbing some of the methanol into the liquid phase. The gas leaving the contacting step is now at about the same temperature and methanol concentration as it was in the feed to the previous bed. The quantity of syngas, however, has been reduced because some of the syngas was converted to methanol. These series of steps are then repeated several more times, each time increasing the conversion of syngas. The number of catalyst beds and liquid contacting stages, along with control of the temperatures, space velocities, and pressure, determines the ultimate level of conversion of syngas through the reactor system.

In this invention, it is preferred to maximize the conversion at each bed of catalyst so as to approach equilibrium as closely as possible. The approach to equilibrium conversion can be expressed as an approach temperature to an equilibrium composition. For any given mixture of syngas reactants and methanol product, a temperature can be calculated where the thermodynamic driving force for further reaction is zero. The difference between this calculated equilibrium temperature and the actual process temperature is the approach to equilibrium. A low approach to equilibrium is particularly desirable. Preferably, the reaction process is carried out at an approach to equilibrium temperature of not greater than 15° C., more preferably not greater than 10° C., and most preferably not greater than 5° C.

Approach to equilibrium temperature can be controlled in this invention by controlling weight hourly space velocity, methanol content in the feed to one or more catalyst beds, the actual reaction temperature, the reactor pressure, or any combination thereof. The extent of conversion at equilibrium in a catalyst bed is favored at lower space velocities, lower temperatures, and lower product (methanol) concentrations in the feed to the one or more catalyst beds. In one embodiment, the weight hourly space velocity (WHSV) through each bed is not greater than 100 $hr^{-1}$, preferably not greater than 50 $hr^{-1}$, and more preferably not greater than 10 $hr^{-1}$. In one embodiment, the methanol content in the gas being sent to each reactor bed is not greater than 60 mol %, preferably not greater than 55 mol %, and more preferably not greater than 50 mol %. In one embodiment, the average temperature of each bed is not greater than 240° C., preferably not greater than 230° C., and more preferably not greater than 220° C.

This invention maximizes conversion at each catalyst bed by flowing the gas exiting the previous catalyst bed through a liquid layer that both cools the flowing gas and extracts at least a portion of the methanol. As the methanol concentration of the gas is removed and the gas is cooled, additional synthesis gas components (i.e., carbon monoxide and hydrogen, and, optionally, carbon dioxide) can be more easily converted to methanol. In one embodiment, the average temperature of the cooled gas (i.e., the gas flowed across the liquid layer and exits the liquid layer) is not greater than about 210° C., preferably not greater than about 200° C., and more preferably not greater than about 190° C. In another embodiment, the methanol content of the cooled gas is not greater than about 60 mol %, preferably not greater than about 55 mol %, and more preferably not greater than about 50 mol %.

Because the sequential reaction and extraction steps of this process can be carefully controlled, the final conversion of syngas is high. Preferably, the reaction process is continued until overall conversion of CO is at least about 50%, more preferably at least about 60%, and most preferably at least about 75%.

The liquid layer that is used to cool the gas and extract methanol can be any composition effective to absorb methanol from the gas phase into the liquid phase. Preferably, the liquid layer contains methanol that has been removed from the gas that has been produced. It is particularly preferred to flow the liquid in an overall countercurrent direction relative to the flowing gas. As the liquid continues toward its ultimate direction, it will become more enriched in methanol (unless methanol itself is used as the absorbing liquid, in which case the composition does not substantially change). At a final desired stage in the reaction process, the methanol product is then recovered. If desired, however, methanol can be recovered from any one or more of the liquid layers as they are flowed in their countercurrent direction.

In one embodiment, at least a portion of the recovered methanol product is re-used in the process. In particular, at least a portion of the methanol in the recovered product is cooled and the cooled methanol product is added back to at least one of the liquid layers that is flowing countercurrently to the flowing gas compositions. This enables the gas flowing between each bed of catalyst to be sufficiently cooled as the overall reaction continues through each stage of the process. The temperature of the cooled methanol is selected such that, after contacting with the gas, the gas temperature falls into the desired ranges stated above.

It is particularly desirable for the liquid to minimize contact with the catalyst and unreacted syngas at the same time. The presence of liquid methanol on the catalyst will reduce the potential conversion of syngas to methanol. It is also possible for some of the methanol to undergo the reverse reaction and decompose back to syngas.

Although the liquid layers are flowed in an overall countercurrent direction relative to the flowing gas, contact of the liquid with catalyst can be minimized by flowing the liquid across only a minimal horizontal layer of the catalyst rather than down through the entire catalyst bed. In one embodiment, at least one liquid layer is flowed across an upper portion of a corresponding catalyst bed (e.g., the liquid is flowed substantially horizontally across an upper portion of the catalyst bed as the gas flowing through the same catalyst bed flows in a substantially vertical direction). Preferably, at least a majority of the liquid layers in the reaction vessel are flowed across the upper portions of each of the corresponding catalyst beds.

The liquid can be substantially prevented from contacting the catalyst or flowing through any one of the catalyst beds by any appropriate means. Examples of such means include: (i) the use of any standard distillation column tray, which includes sieve trays, valve trays, and bubble cap trays, designed to allow vapor to flow up through the tray, and substantially prevent liquid from flowing down through the tray; and (ii) using the catalyst bed itself to prevent liquid from flowing downward through the catalyst bed by selecting a vapor velocity traveling upward through the bed that does not allow substantial liquid to flow downward through the catalyst bed. In this embodiment, the liquid is substantially prevented from flowing through the bed by selecting a gas velocity that achieves a pressure drop through the catalyst bed of at least 0.01 psi/ft (0.23 kPa/m) of bed height, preferably at least 0.05 psi/ft (1.1 kPa/m) of bed height, and more preferably at least 0.1 psi/ft (2.3 kPa/m) of bed height. This pressure drop can be calculated by those skilled in the art by means of the Ergun equation (see for example, Bennett & Myers, *Momentum, Heat, and Mass Transfer*, 2nd Ed. McGraw Hill, New York (1974)).

The reaction process can be carried out in one or more vessels. For example, each catalyst bed can be contained in its own vessel and each liquid layer can flow through a vessel separate from the catalyst containing vessels. In one embodiment, a single vessel is used containing a plurality of catalyst beds spaced apart from one another. In a particular embodiment, synthesis gas is flowed in an upward direction and methanol is formed as the gas flows through each catalyst bed. A methanol containing liquid layer is also flowed across one or more, preferably each, of the catalyst beds, and in an overall countercurrent direction such that gas exiting the beds flows through each liquid layer, and a substantial portion of the methanol that is in the exiting gas is absorbed in the liquid layer. The liquid layers are also maintained at an average temperature that cools the gas as it flows through each layer. In a countercurrent flow arrangement, the liquid is flowed so as to contact the gas exiting the preceding bed of methanol synthesis catalyst. An overall countercurrent flow may be accomplished by installing one or more downcomers at each catalyst bed so that the liquid is flowed across the catalyst bed and down through the downcomer.

In an optional embodiment of the invention, fresh syngas is partially converted to methanol prior to feeding the plurality of beds. Any type of reactor may be employed in this pre-conversion step. For example, adiabatic fixed beds, tubular reactors, and fluid bed reactors can be used to convert at least a portion of the fresh syngas to methanol. For example, any of the reactor types described in U.S. Pat. No. 4,968,722 can be used. The multi-bed reactor used according to invention is then used to convert more of the unconverted syngas to additional methanol. The partially-converted syngas that is recovered from the pre-reaction vessel is sent to the plurality of catalyst beds and flowed in a direction countercurrent to the flowing liquid to continue the methanol conversion reaction to the desired conversion product. In this manner, the methanol contained in the product from the pre-conversion isothermal reactor is absorbed into the countercurrent flowing liquid stream in the vessel containing the plurality of catalyst beds. The vapor feed to the first of the plurality of catalyst beds is therefore reduced in methanol content, thus allowing the reactants to undergo further conversion to methanol in the catalyst bed.

Commercial processes that manufacture syngas inherently contain small quantities of inert materials such as nitrogen and methane. As the conversion of syngas ($H_2$, CO, and $CO_2$) increases, the concentration of these inert species generally increase. Thus, the concentration of reactants generally decrease as the conversion increases, even when methanol is removed between each catalyst bed as described above. In order to achieve an overall high conversion of CO in the process, it is desirable to operate with a decreasing temperature profile as the syngas travels up the column. The temperature should be somewhat higher at the bottom where the concentration of reactants is high, as reaction rates will be higher and the equilibrium conversion constraints are not so great. The temperature should be somewhat lower towards the top of the column where reactants have been consumed and the concentration of inerts builds up. Lower temperatures allow higher thermodynamic conversions to occur in the diluted reaction mixture. The average bed temperature in the first (bottom) bed is preferably at least 5° C. hotter than the last (top) bed, more preferably at least 10° C. hotter, and most preferably at least 15° C. hotter.

The liquid that is used to form the liquid layers used in this invention not only absorbs methanol but cools the product gases as they flow through each layer. As stated above, the liquid is preferably maintained at a temperature such that the gases that are flowed through each catalyst bed exhibit an overall temperature profile in which the average temperature of each catalyst bed decreases in the direction of gas flow. Thus, each liquid layer is at an average temperature that cools the gas flowing through it. In one embodiment, each liquid layer is maintained at an average temperature of not greater than 250° C. Preferably, each liquid layer is at an average temperature of not greater than 240° C., more preferably not greater than 230° C., and most preferably not greater than 220° C.

In another embodiment, none of the beds of methanol synthesis catalyst has an inlet temperature greater than 240° C. Preferably, none of the beds of methanol synthesis catalyst has an inlet temperature greater than 220° C.

In this invention, it is preferred that each catalyst bed is arranged in series. In particular embodiments, it is also preferred that, on average, no catalyst bed has an inlet temperature greater than that of the previous bed in series. That is, on average the temperature decreases as the gas flows up the column, but on occasion, the temperature profile can be discontinuous due to the number and locations of pumparound loops that are used to cool certain beds. Thus, in one embodiment, at least some of the methanol is withdrawn from the column, cooled, and pumped back into the column at a desired location to cool any bed below the location at which the cooled methanol is injected. More than one pumparound can be used.

A wide variety of pressures can be accommodated in carrying out the process of the invention. Preferably, the gases and liquid layers are flowed in one or more vessels, each at a pressure of at least 30 bar, more preferably at least 50 bar, still more preferably at least 70 bar, and most preferably at least 90 bar. Preferably, the gases and liquid layers are flowed in one or more vessels, each at a pressure of not greater than 200 bar, preferably not greater than 150 bar, and more preferably not greater than 120 bar.

II. Process Feed

As in a typical methanol producing process, synthesis gas (syngas) is used in the feed as feed in the initial reaction step of this invention. Desirably, the synthesis gas used in the initial reaction step has a molar ratio of hydrogen ($H_2$) to carbon oxides ($CO+CO_2$) in the range of from about 0.5:1 to about 20:1, preferably in the range of from about 1:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas, and preferably less than 20% by weight, more preferably less than 10% by weight.

Desirably, the stoichiometric molar ratio is sufficiently high so as maintain a high yield of methanol, but not so high as to reduce the volume productivity of methanol. Preferably, the synthesis gas fed to the methanol synthesis process has a stoichiometric molar ratio (i.e., a molar ratio of ($H_2$—$CO_2$)/($CO+CO_2$)) of from about 1.0:1 to about 2.7:1, more preferably from about 1.5 to about 2.5, more preferably a stoichiometric molar ratio of from about 1.7:1 to about 2.5:1.

III. Catalyst

Preferably, the methanol synthesis catalyst used in the process of this invention includes an oxide of at least one element selected from the group consisting of copper, silver, zinc, boron, magnesium, aluminum, vanadium, chromium, manganese, gallium, palladium, osmium and zirconium. More preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

IV. Other Extractants

An extractant or solvent can be added to the methanol layer so as to enhance or suppress the volatility of the methanol being removed from the gas streams or as aids in extracting the methanol from the gases. Extractants which can be used in this invention are liquids at 1 atm. These extractants also desirably have an average boiling point at atmospheric pressure of at least 100° F. (38° C.), preferably at least 120° F. (49° C.), and more preferably at least 150°

F. (66° C.). Average boiling point, as defined herein, takes into account the boiling point of each compound in the extractant on a weight average basis. For example, an extractant containing 90 wt. % of a compound having a boiling point of 100 degrees and 10 wt. % of a compound having a boiling point of 200 degrees would have an average boiling point of 110 degrees. The extractants are also desirably polar compositions. Examples of such compositions include at least one composition selected from the group consisting of water, monohydric alcohols, and polyhydric alcohols. Preferred monohydric alcohols, in addition to methanol, include ethanol and propanol. Preferred polyhydric alcohols include glycols. Preferred glycols include ethylene glycol and tri-ethylene glycol.

V. Recovery and Further Processing of Methanol Product

After reaction, the methanol product can be recovered and used "as is," or it can be further processed if desired. Processing can be accomplished using any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol present.

In one embodiment, the recovered methanol product is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another embodiment, the recovered methanol product is sent from the methanol synthesizing unit or vessel to a distillation system. The distillation system contains one or more distillation columns which are used to further separate the desired methanol composition from water and hydrocarbon by-product streams. Desirably, the methanol composition that is separated from the crude methanol comprises a majority of the methanol contained in the methanol product prior to separation.

In one embodiment, the distillation system includes a step of treating the recovered methanol product steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles are taken overhead and methanol liquid as bottoms. The second is a "rectifying column" from which methanol product is taken as an overhead stream or at a high level, and water is removed as a bottoms stream. In this embodiment, the rectifying column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60 % w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or rectifying column. The semi-crude methanol is passed to a rectifying column, from which methanol product is taken overhead or at a high level. Preferably, water or aqueous methanol is taken as a bottoms stream.

Alternatively, undesirable by-products are removed from the crude methanol stream from the methanol synthesis reactor by adsorption. In such a system, fusel oil can be recovered by regenerating the adsorbent.

VI. Use of the Methanol Composition in the Manufacture of Olefins

The methanol product composition of this invention can be used as feed for any conventional process. Examples of such uses include the manufacture of methyl tertiary butyl alcohol (MTBE) for use in reformulated gasolines and oxygenated fuels; the use of methanol as a fuel for fuel cells, use as feedstock to make olefins, and for use in making acetic acid and formaldehyde.

The methanol product stream of this invention is particularly suited for conversion to olefins, particularly ethylene and/or propylene. The methanol product stream can be fed directly to an olefin conversion process or it can be transported in large quantities over great distances and converted to olefins.

According to this invention, the methanol product can be produced in large scale quantities for conversion to olefins, which is of great advantage for further conversion of the olefins to polyolefins such as polyethylene and polypropylene. Advantageously, this invention allows for at least 100,000 metric tons of methanol product per year. Preferably, production is at least 500,000 metric tons per year, more preferably at least 1 million metric tons per year, and most preferably at least 2 million metric tons per year.

In one embodiment, the methanol stream of the invention is separated from a crude methanol stream, and transported to a location geographically distinct from that where the methanol composition was separated from the crude methanol stream. Preferably, the methanol composition of this invention is loaded into a vessel, and the vessel is transported over a body of water to a storage facility. The methanol can be easily transported at least 100, 500 or 1,000 miles or more. Once arriving at the storage facility, the methanol composition is delivered to a storage tank. From the storage tank, the methanol composition is ultimately sent to an olefin conversion unit for conversion to an olefin product. The methanol composition is preferably, loaded onto a ship, with the ship able to contain at least 20,000 tons, preferably at least 40,000 tons, and more preferably at least 80,000 tons.

An advantage of being able to transport the methanol composition is that the units which produce the methanol do not have to be located in close geographic proximity to the olefin conversion unit. This makes it possible to use remote gas reserves. These remote gas reserves would be used as feed for the methanol manufacturing facility. The methanol made at these remote sites can then be easily transported to a suitable location for conversion to olefins. Since olefins and polyolefins (i.e., plastics) demands are typically low at the remote gas sites, there will generally be a desire to transport methanol to high olefins and plastic demand areas. Methanol is routinely transported in vessels that are similar to those that transport crude oil and other fuels. Examples of locations of remote gas reserves include the coastline of west Africa, northwest Australia, in the Indian Ocean, and the Arabian Peninsula. Examples of locations of preferred sites to convert methanol to other products such as olefins include the U.S. Gulf coast and northwest Europe.

VII. EXAMPLES OF DIFFERENT EMBODIMENTS

Example 1

An example of one embodiment of the invention is shown in the FIG. 1. In the FIG. 1, syngas is sent by way of a line 10 to a pre-conversion reactor 12. A portion of the syngas is converted to methanol, and this gaseous product is sent by way of a line 14 to a vessel 16 containing a plurality of beds of methanol synthesis catalyst 18a, 18b and 18c. After the partially converted syngas enters the vessel 16, it flows in an upward direction and flows through the catalyst bed 18a, where conversion of remaining syngas components to methanol continues.

As the gas flowing through catalyst bed 18a, exits the bed, the exiting gas flows through liquid layer 20a. The liquid layer 20a is flowed across an upper portion of the catalyst bed 18a. That is, the liquid layer 20a is flowed substantially horizontally across an upper portion of the catalyst bed 18a as the gas flowing through the catalyst bed 18a flows in a substantially vertical direction. The liquid layer 20a extracts at least a portion of the methanol from the exiting gas and also cools the gas.

Likewise, the gas continues its upward flow through catalyst bed 18b, liquid layer 20b, catalyst bed 18c and liquid layer 20c. The gas then flows out of vessel 16 through a line 32, and the gas is cooled by an exchanger 34 to condense a large portion, if not all, of any methanol that has not been extracted as the gas flowed through liquid layer 20c. The cooled gas is sent to settler 36, where non-condensed components such as carbon monoxide, hydrogen, nitrogen and methane exit by way of purge line 40. Condensed liquid is recycled to the vessel by way of line 38 to replenish the liquid in the layer 20c as the liquid flows in a overall direction that is countercurrent to the gas flow by way of lines 22c, 22b and 22a. Methanol product is then recovered from the vessel 16 by way of a line 24.

Temperatures within the vessel 16 are further controlled by recycling cooled methanol product to the vessel at any desired point. In the FIG. 1, a portion of the methanol product is taken through a line 26 and cooled by way of an exchanger 28. The cooled methanol product is then returned to the vessel 16 by way of a line.

Example 2

A computer-based model (Pro/II® by Simulation Sciences) was used to simulate one embodiment of the invention similar to that shown in the FIG. 1. In the simulation, however, 11 catalyst beds were housed in the reaction vessel. The beds were designated as beds R1-R11, starting from the bottom of the reaction vessel as R1, and continuing up to the top as R11. Reflux from the settler vessel was returned to the reaction vessel between beds R10 and R11. In addition, a portion of the methanol product was recovered and cooled for return to the reaction vessel to further control temperatures within the reaction vessel. However, the cooled methanol product was returned by way of three different"pump around" (P/A) lines, designated P/A#1, P/A#2 and P/A#3. P/A#1 was returned to the vessel between beds R7 and R8. P/A#2 was returned to the vessel between beds R5 and R5. P/A#3 was returned to the vessel between beds R4 and R5.

Partial conversion of syngas feed over the initial pre-conversion reactor was carried out at 67% $CO_x(CO+CO_2)$ and 64% $H_2$ conversion. Each of the 11 catalyst beds in the countercurrent flow vessel was allowed to approach equilibrium conversion at adiabatic conditions with a 10° C. approach to equilibrium conversion. In particular, the data in Tables 1-3 show that, comparing the flow rates of CO and $H_2$ in the"Syngas Feed" with the"Purge", a high overall conversion of syngas was achieved. The overall conversion of synthesis gas was calculated to be 93% for $CO_x$ and 89% for $H_2$. Further details of the simulation are shown in Tables 1-3.

TABLE 1

(Stream Characteristics)

| Stream Characteristic | Syngas Feed | Gas to Vessel | Reflux | Purge | Bottoms | P/A #2 | P/A #1 | P/A #3 |
|---|---|---|---|---|---|---|---|---|
| Phase | Vapor | Vapor | Liquid | Vapor | Liquid | Liquid | Liquid | Liquid |
| Temp (° C.) | 178.9 | 240.0 | 48.0 | 48.0 | 195.0 | 48.0 | 48.0 | 48.0 |
| Press. (bar) | 100 | 100 | 100 | 100 | 100 | 100 | 100 | 100 |
| Flowrate (kg-mol/hr) | 97.8 | 57.3 | 7.1 | 12.2 | 29.4 | 25.0 | 15.0 | 35.0 |
| Total Mass Rate (kg/hr) | 1101.1 | 1101. | 218.4 | 178.2 | 922.3 | 783.3 | 470.0 | 1096.6 |
| Total Mol Wt. | 11.3 | 19.2 | 31.0 | 14.7 | 31.3 | 31.3 | 31.3 | 31.3 |

TABLE 2

(Stream Composition; mole %)

| Component | Syngas Feed | Gas to Vessel | Reflux | Purge | Bottoms | P/A #2 | P/A #1 | P/A #3 |
|---|---|---|---|---|---|---|---|---|
| $H_2O$ | 0.35 | 0.26 | 7.88 | 0.02 | 1.66 | 1.66 | 1.66 | 1.66 |
| $N_2$ | 2.06 | 3.51 | 0.44 | 16.17 | 0.15 | 0.15 | 0.15 | 0.15 |
| CO | 29.01 | 13.82 | 0.05 | 1.50 | 0.88 | 0.88 | 0.88 | 0.88 |
| $CO_2$ | 2.00 | 3.76 | 4.44 | 13.45 | 0.55 | 0.55 | 0.55 | 0.55 |
| Methane | 1.91 | 3.25 | 1.01 | 14.81 | 0.22 | 0.22 | 0.22 | 0.22 |
| Methanol | 0 | 35.36 | 85.07 | 1.04 | 94.99 | 94.99 | 94.99 | 94.99 |
| $H_2$ | 64.68 | 40.04 | 1.11 | 53.00 | 1.56 | 1.56 | 1.56 | 1.56 |

TABLE 3

(Stream Composition Flow Rate; kg-mol/hr)

| Component | Syngas Feed | Gas to Vessel | Reflux | Purge | Bottoms | P/A #2 | P/A #1 | P/A #3 |
|---|---|---|---|---|---|---|---|---|
| $H_2O$ | 0.34 | 0.15 | 0.56 | 0 | 0.49 | 0.41 | 0.25 | 0.58 |
| $N_2$ | 2.01 | 2.01 | 0.03 | 1.97 | 0.04 | 0.04 | 0.02 | 0.05 |
| CO | 28.38 | 7.92 | 0 | 0.18 | 0.26 | 0.22 | 0.13 | 0.31 |
| $CO_2$ | 1.96 | 2.15 | 0.31 | 1.64 | 0.16 | 0.14 | 0.08 | 0.19 |
| Methane | 1.86 | 1.86 | 0.07 | 1.80 | 0.06 | 0.05 | 0.03 | 0.08 |
| Methanol | 0 | 20.26 | 6.00 | 0.13 | 27.96 | 23.75 | 14.25 | 33.24 |
| $H_2$ | 63.28 | 22.95 | 0.08 | 6.45 | 0.46 | 0.39 | 0.23 | 0.55 |

The principles and modes of operation of this invention have been described above with reference to various exemplary and preferred embodiments. As understood by those of skill in the art, the overall invention, as defined by the claims, encompasses other preferred embodiments not specifically enumerated herein.

The invention claimed is:

1. A process for producing methanol, comprising:
   flowing gas containing carbon monoxide, carbon dioxide and hydrogen through a plurality of beds of methanol synthesis catalyst so as to form methanol in the flowing gas; and
   flowing gas exiting each of the beds through separate liquid layers containing methanol to remove at least a portion of the methanol from the gas and cool the gas, wherein the separate liquid layers are flowed in an overall countercurrent direction relative to the flowing gas, and the flow of at least one liquid layer is across an upper portion of a corresponding catalyst bed.

2. The process of claim 1, further comprising recovering methanol product from any one or more of the liquid layers.

3. The process of claim 2, further comprising cooling at least a portion of the recovered methanol product and adding at least a portion of the cooled methanol product to at least one of the liquid layers flowing in countercurrent direction relative to the gas compositions.

4. The process of claim 1, wherein each liquid layer is at an average temperature that cools the gas flowing across it.

5. The process of claim 4, wherein each liquid layer is at an average temperature of not greater than 250° C.

6. The process of claim 1, wherein the gases and liquid layers are flowed in a vessel at a pressure of at least 30 bar.

7. The process of claim 1, wherein the methanol synthesis catalyst includes an oxide of at least one element selected from the group consisting of copper, silver, zinc, boron, magnesium, aluminum, vanadium, chromium, manganese, gallium, palladium, osmium and zirconium.

8. The process of claim 1, wherein the liquid layers contain at least one additional methanol adsorbent selected from the group consisting of water, monohydric alcohols, and polyhydric alcohols.

9. The process of claim 1, wherein each bed has an average temperature in a linear arrangement or profile that differs from one another in a range of from 0° C. to 10° C.

10. The process of claim 1, wherein the methanol is formed at an approach to equilibrium temperature of not greater than 15° C.

11. The process of claim 1, wherein the gas is flowed at a weight hourly space velocity of not greater than 100 $hr^{-1}$.

12. The process of claim 1, wherein the cooled gas has an average temperature of not greater than 210° C.

13. The process of claim 1, wherein the methanol is continued to form until overall conversion of the carbon monoxide is at least about 50%.

14. The process of claim 1, wherein the gas is flowed at a gas velocity that achieves a pressure drop through each catalyst bed of at least 0.01 psi/ft of bed height.

15. A process for producing methanol, comprising:
   flowing gas containing carbon monoxide, carbon dioxide and hydrogen through a bed of methanol synthesis catalyst to form gas containing methanol;
   flowing the gas containing methanol through a liquid layer containing methanol to remove at least a portion of the methanol from the flowing gas and cool the gas, wherein the liquid layer is flowed substantially horizontally across an upper portion of the catalyst bed as the gas flowing through the catalyst bed flows in a substantially vertical direction; and
   recovering methanol product from the liquid layer.

16. The process of claim 15, wherein the methanol synthesis catalyst includes an oxide of at least one element selected from the group consisting of copper, silver, zinc, boron, magnesium, aluminum, vanadium, chromium, manganese, gallium, palladium, osmium and zirconium.

17. The process of claim 15, wherein the liquid layer contains at least one additional methanol adsorbent selected from the group consisting of water, monohydric alcohols, and polyhydric alcohols.

18. The process of claim 15, wherein the methanol is formed at an approach to equilibrium temperature of not greater than 15° C.

19. The process of claim 15, wherein the gas and liquid layer are flowed in a vessel at a pressure of at least 30 bar.

20. The process of claim 15, wherein the gas is flowed at a weight hourly space velocity of not greater than 100 $hr^{-1}$.

21. The process of claim 15, wherein the cooled gas has an average temperature of not greater than 210° C.

22. The process of claim 15, wherein, the methanol is continued to form until overall conversion of the carbon monoxide is at least about 50%.

23. The process of claim 15, wherein the gas is flowed at a gas velocity that achieves a pressure drop through the catalyst bed of at least 0.01 psi/ft of bed height.

* * * * *